United States Patent [19]

Tobler et al.

[11] Patent Number: 4,507,146
[45] Date of Patent: Mar. 26, 1985

[54] 2,4-DIAMINO-6-HALO-5-TRIFLUOROMETHYLPYRIMIDINES HAVING HERBICIDAL ACTIVITY

[75] Inventors: Hans Tobler, Allschwil; Karl Hoegerle, Basel, both of Switzerland

[73] Assignee: Ciba-Geigy Corporation, Ardsley, N.Y.

[21] Appl. No.: 562,660

[22] Filed: Dec. 19, 1983

[30] Foreign Application Priority Data

Dec. 28, 1982 [CH] Switzerland .................. 7588/82

[51] Int. Cl.³ .................. A01N 43/48; C07D 239/02
[52] U.S. Cl. .................. 71/92; 544/323; 544/324
[58] Field of Search .................. 544/324, 323; 71/92

[56] References Cited

U.S. PATENT DOCUMENTS

| Re. 31,136 | 2/1983 | Treves | 544/323 |
| 3,325,496 | 6/1967 | Critchley et al. | 544/323 |
| 4,055,411 | 10/1977 | Fischer | 71/92 |

FOREIGN PATENT DOCUMENTS

| 1148950 | 6/1983 | Canada . |
| 0000681 | 2/1979 | European Pat. Off. . |
| 2006145 | 10/1970 | Fed. Rep. of Germany . |
| 2132963 | 1/1973 | Fed. Rep. of Germany . |
| 2310334 | 9/1973 | Fed. Rep. of Germany . |
| 859716 | 1/1961 | United Kingdom .................. 544/323 |

OTHER PUBLICATIONS

Hasek et al., J.A.C.S. 82, 543 (1960).
Winkelmann, "Über einige Derivate des 2,4,6-trichloro-pyrimidins", *J. prakt. Chem.* 115, 292-314 (1927).
Smith, "Chemie des Schwefeltetrafluorids", *Angew Chem.* 74, 742-750 (1962).

*Primary Examiner*—Donald G. Daus
*Assistant Examiner*—Cecilia Shen
*Attorney, Agent, or Firm*—Frederick H. Rabin

[57] ABSTRACT

2,4-Diamino-6-halo-5-trifluoromethylpyrimidines of the formula

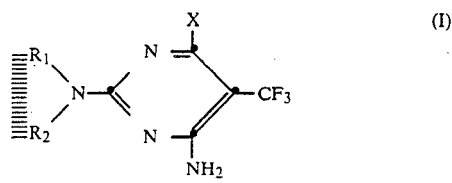

wherein X is a halogen atom, especially chlorine or fluorine, and $R_1$ and $R_2$ independently of one another are each hydrogen, $C_1$–$C_6$-alkyl or $C_3$–$C_6$-cycloalkyl, or together form a $C_3$–$C_7$-alkylene bridge, have outstanding selective-herbicidal properties, and are suitable for controlling weeds in crops of cultivated plants, such as maize, cereal or soya-bean. They are produced by aminating 2,4,6-trihalo-5-trifluoromethylpyrimidine, which for its part is obtainable by fluorination of 2,4,6-trihalopyrimidine-5-carboxylic acid. The 2,4,6-trihalo-5-carboxylic acids are novel intermediates, and are obtained by oxidizing 2,4,6-trihalo-2-methyl-, -halomethyl- or -formyl-pyrimidine in sulfuric acid by means of chromium trioxide.

9 Claims, No Drawings

2,4-DIAMINO-6-HALO-5-TRIFLUOROMETHYL-PYRIMIDINES HAVING HERBICIDAL ACTIVITY

The present invention relates to novel 2,4-diamino-6-halo-5-trifluoromethylpyrimidines having herbicidal activity, to the production of these novel pyrimidines, to a herbicidal composition containing them as active ingredients, and to the use thereof for controlling weeds, particularly for the selective control of weeds in cultivated crops. The invention embraces also novel intermediates and their production.

Pyrimidines having a herbicidal action or an action otherwise influencing plant physiology have become known in large numbers; relevant publications which may be mentioned are for example: J. prakt. Chemie 115, p. 292 (1927), German Offenlegungsschriften Nos. 2,006,145 and 2,356,644, or more recently also the European published Patent Application Nos. 681 and 24 260.

The 2,4-diamino-6-halo-5-trifluoromethylpyrimidines of the present invention correspond to the general formula I

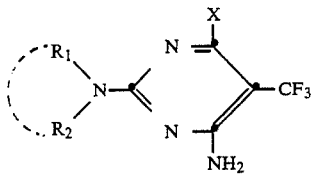

wherein
X is a halogen atom, especially chlorine or fluorine,
$R_1$ and $R_2$ independently of one another are each hydrogen, $C_1$-$C_6$-alkyl or $C_3$-$C_6$-cycloalkyl, or together form a $C_3$-$C_7$-alkylene bridge.

The alkyl groups comprise all straight-chain or branched-chain groups; and the cycloalkyl groups can be unsubstituted or substituted by $C_1$-$C_3$-alkyl.

The pyrimidine compounds of the formula I are novel compounds. They have marked selective-herbicidal properties in general, and prove to be particularly advantageous for the control of weeds in crops of cultivated plants, especially in maize and cereal crops, but also in crops of soya bean, cereals such as barley and oats, as well as sugar beet. A total herbicidal action results however when the amount applied is sufficiently great. The novel active substances of the invention can be applied both in the pre-emergence process and in the post-emergence process, and the amounts used can vary within wide limits, for example between 0.1 and 10 kg of active substance per hectare; preferably however the employed amount of active substance is between 0.5 and 5 kg per hectare. But in some cases a good selective herbicidal action has been observed even with an applied amount of only 0.25 kg per hectare.

The compounds of the formula I also have an action regulating the growth of plants, effecting for example a reduction in the growth of cereals, only the vegetative growth however being reduced. The resulting cereals then have shorter but stronger stems which are not so easily bent or flattened by wind and storm. At the same time the generative growth remains unaffected; indeed, by virtue of better resistance to climate, increases in yield can be obtained.

Preferred pyrimidines of the formula I are those wherein X is chlorine or fluorine, especially fluorine, and $R_1$ and $R_2$ have the meanings defined in the foregoing. The following compounds are especially worthy of note:

2,4-diamino-6-fluoro-5-trifluoromethylpyrimidine,
4-amino-6-fluoro-2-methylamino-5-trifluoromethylpyrimidine and
4-amino-2-dimethylamino-6-fluoro-5-trifluoromethylpyrimidine.

The final stages for producing 2,4-diamino-6-halo-5-trifluoropyrimidines are carried out in a manner known per se.

A 2,4,6-trihalo-5-trifluoromethylpyrimidine of the formula II

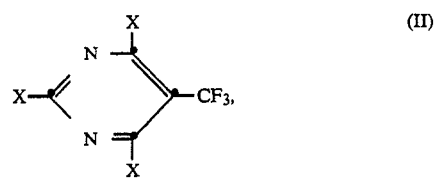

wherein X is a halogen atom, preferably chlorine or fluorine, is treated in a solvent inert to the reactants, at a temperature of between −10° and +50° C., with 2-3 mols of an aqueous solution of an amine of the formula III

wherein $R_1$ and $R_2$ have the meanings defined in the foregoing, and the final product is isolated by separating off the aqueous phase and concentrating the solvent by evaporation. There is thus formed mainly 2-amino-4,6-dihalo-5-trifluoromethylpyrimidine of the formula IV

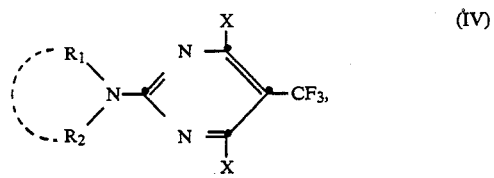

wherein $R_1$, $R_2$ and X have the aforesaid meanings, besides smallish proportions of 4-amino-2,6-dihalo-5-trifluoromethylpyrimidine and 2,4-diamino-6-halo-5-trifluoromethylpyrimidine, which can be readily separated by chromatography. The 2-amino-4,6-dihalo-5-trifluoromethylpyrimidine of the formula IV is then treated in a solvent inert to the reactants, at a temperature of between +20° and +100° C., with 2-3 mols of aqueous ammonia solution, by which means is obtained, after separation of the aqueous phase, 2,4-diamino-6-halo-5-trifluoromethylpyrimidine of the formula I as the main product, together with small amounts of 4,6-diamino-2-halo-5-trifluoromethylpyrimidine and stereoisomeric 2,4-diamino-6-halo-5-trifluoromethylpyrimidine, wherein the amino groups have exchanged positions, as by-products, which can easily be separated by chromatography.

The process for producing the novel 2,4-diamino-6-halo-5-trifluoromethylpyridine of the formula I accordingly comprises treating a 2,4,6-trihalo-5-trifluoromethylpyrimidine of the formula II in an inert solvent, at a temperature of between −10° and +50° C., with 2-3 mol equivalents of an aqueous solution of an amine of the formula III; isolating the formed 2-amino-4,6-dihalo-5-trifluoromethylpyrimidine; treating this in an inert solvent, at a temperature of between +20° and +100° C., with 2–3 mol equivalents of an aqueous ammonia solution; and subsequently isolating the final product.

Suitable solvents are advantageously hydrocarbons, halogenated hydrocarbons, or ethers, such as toluene, benzene, chloroform, methylene chloride, ethylene chloride, ether, dioxane and tetrahydrofuran, or mixtures of these with one another. It is of advantage also if the solvent is not miscible with water, since the intermediate or final product is then readily isolated by discarding the aqueous phase and concentrating the organic phase.

The starting materials and intermediates required for this production process and the production thereof are for the most part novel, and they likewise form subject matter of the present invention.

The 2,4,6-trihalo-5-trifluoromethylpyrimidines of the formula II are produced for example by starting with a 2,4,6-trihalo-2-formyl-pyrimidine, known from the German Offenlegungsschrift No. 2,310,334, or with a similar trihalopyrimidine of the formula V

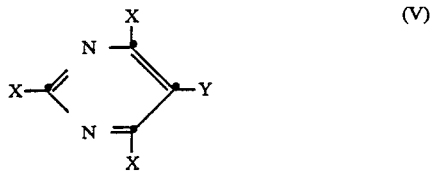
(V)

wherein X is a halogen atom, preferably chlorine, and Y is the methyl or formyl group or a halomethyl group, and oxidising this compound at a temperature of between 10° and 100° C., preferably between 20° and 50° C., in the presence of chromium trioxide, or of a salt which forms chromium trioxide under the reaction conditions, and in the presence of fuming or at least 98% sulfuric acid, to give the 2,4,6-trihalopyrimidine-5-carboxylic acid of the formula VI

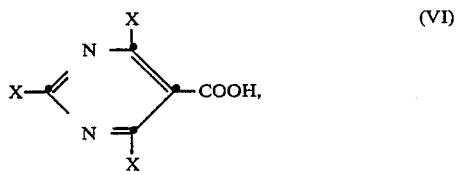
(VI)

wherein X is a halogen atom, and optionally subjecting the product obtained to a halogen exchange reaction.

The compounds of the formula VI, particularly the corresponding chlorine derivatives, can be produced by the process according to the invention in a simple and economical manner and with good to very good yields. It was possible to produce 2,4-dihalopyrimidine-5-carboxylic acid halides hitherto only in a very complicated manner from cyanoacetylurea with the Bredereck complex of dimethyl sulfate and dimethylformamide by way of 5-cyanouracil and uracil-5-carboxylic acid [cp. for example British patent specifications Nos. 1,123,762 and 1,182,086]. In the German Auslegeschrift No. 2,132,963, 2,4,6-trichloropyrimidine-5-carboxylic acid chloride is mentioned by name as reactive component; it is however not stated how this compound could be produced.

Salts releasing chromium trioxide under the reaction conditions are for example potassium chromate and potassium or sodium dichromate. The reaction is performed preferably in the presence of chromium trioxide.

The fuming sulfuric acid used is preferably one having an $SO_3$ content of 20–80%. Particularly preferred is fuming sulfuric acid having an $SO_3$ content of 25%. The sulfuric acid serves in the process as solvent; it can however be diluted with a solvent inert and non-oxidising under the reaction conditions, such as with carbon tetrachloride, tetrachloroethane, and so forth.

The starting products of the formula V are known, and can be produced in a manner known per se.

Preferably used as compound of the formula V is 5-formyl-2,4,6-trichloropyrimidine, 5-methyl-2,4,6-trichloropyrimidine or 5-chloromethyl-2,4,6-trichloropyrimidine.

Compounds of the formula VIa wherein X is a halogen atom, preferably chlorine or bromine, R is hydrogen and Y is carboxyl or chlorocarbonyl

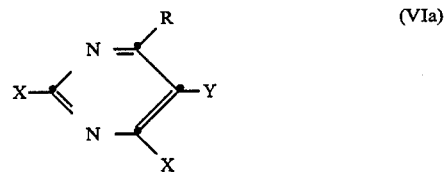
(VIa)

can likewise be converted into compounds of the formula VI or into the corresponding acid halides by treating these first-mentioned compounds at a temperature of between 20° and 350° C., in the presence of active charcoal and a Friedel-Crafts catalyst, with an agent introducing chlorine, fluorine or bromine. Acids of the formula VI thus obtained or acid halides thereof, wherein at least one of the X symbols is chlorine, can if required also be subjected to a halogen exchange reaction. Preferably performed is the after-chlorination of the compound of the formula VIa in which R is hydrogen, X is chlorine and Y is chlorocarbonyl.

Suitable Friedel-Crafts catalysts for the above reaction are for example: iron(II)chloride, iron(III)chloride, antimony(V) chloride and tin(II) chloride. The catalyst preferably used is iron(III) chloride in admixture with active charcoal. The reaction temperatures are preferably between 150° and 160° C. The catalyst is generally used in an amount of 1 to 10 mol %, relative to the starting compound of the formula I as defined.

Suitable agents introducing chlorine, fluorine and/or bromine are for example: $Cl_2$, $Br_2$, phosphorus(V)chloride, -bromide and -fluoride, or sulfuryl chloride. An agent introducing chlorine is preferably used, in particular $Cl_2$.

Compounds of the formula VI produced according to the invention, wherein X is chlorine, can if desired be reacted, for the replacement of one or more chlorine atoms, with a brominating or fluorinating agent, such as: phosphorus tribromide, anhydrous hydrogen fluoride, alkali metal fluorides, silver difluoride, antimony(III)fluoride, antimony(V) fluoride or potassium fluorosulfinate. Thus, for example, the compounds of the formula VI, and also VIa, wherein X is chlorine can be converted into the bromine or fluorine analogs by converting the stated compounds of the formula VI by reaction with phosphorus tribromide, which can also serve as solvent, into 2,4-dibromo- or 2,4,6-tribromopyrimidine-5-carboxylic acid bromide; or by converting such compounds by reaction with one of the aforementioned fluorinating agents, optionally in the presence of a high-boiling, aprotic organic solvent, into 2,4-difluoro- or 2,4,6-trifluoropyrimidine-5-carboxylic acid fluoride. Suitable solvents for these halogen exchange reactions are for example: aromatic hydrocarbons, such as toluene and xylenes; N,N-dialkylamides of aliphatic monocarboxylic acids having 1-3 C atoms in the acid part, such as N,N-dimethylformamide, N,N-dimethylacetamide and N,N-diethylacetamide; cyclic ethers and cyclic amides, such as tetrahydrofuran, tetrahydropyran, N-methyl-2-pyrrolidone and N-acetyl-2-pyrrolidone; hexamethylphosphoric acid triamide (hexametapol); N,N,N',N'-tetramethylurea and tetrahydrothiophene dioxide (sulfolane). The reaction temperatures for the halogen exchange reactions are advantageously between 20° and 250° C., preferably between 50° and 150° C.

The invention relates also to the novel 2,4,6-trihalopyrimidine-5-carboxylic acids of the formula VI wherein X is chlorine, fluorine or bromine.

To obtain the 2,4,6-trihalo-5-trifluoromethylpyrimidine starting materials of the formula II, the 2,4,6-trihalopyrimidinecarboxylic acid of the formula VI, or an acid halide thereof, has to be treated for 5-15 hours in an autoclave at a temperature of 50°-200° C. in the presence of 2-10 mol equivalents of sulfur tetrafluoride and 3.4 mol equivalents of hydrofluoric acid as diluent. Such flourinations of the carboxyl group or possibly of a carbonyl halide are known from the literature (cp. Org. Reactions 21 1 ff; Angewandte Chemie 74, 742 (1962) or J. Am. Chem. Soc. 82, 543 (1960)). Likewise known is the 2,4,6-trifluoro-5-trifluoromethylpyrimidine, principally being formed in the process, from J. Chemie. Soc. (C) 1970, 1280.

The invention relates also to herbicidal and plant-growth-regulating compositions containing a novel active ingredient of the formula I, and also to processes for the pre- and post-emergence control of weeds, and for the reduction in growth of monocotyledonous and dicotyledonous plants, particularly that of grasses, tropical cover crops and side shoots of tobacco plants.

The compounds of the formula I are used either in an unmodified form or preferably in compositions, together with auxiliaries customarily employed in formulation practice, and are thus processed, in a known manner, for example into the form of emulsion concentrates, directly sprayable or dilutable solutions, diluted emulsions, wettable powders, soluble powders, dusts or granulates, and also encapsulations in for example polymeric substances. The application processes, such as spraying, atomising, dusting, scattering or pouring, and likewise the type of compositions, are selected to suit the objects to be achieved and the given conditions.

The formulations, that is to say, the compositions or preparations containing the active ingredient of the formula I and optionally a solid or liquid additive, are produced in a known manner, for example by the intimate mixing and/or grinding of the active ingredients with extenders, such as with solvents, solid carriers and optionally surface-active compounds (tensides).

Suitable solvents are: aromatic hydrocarbons, preferably the fractions $C_8$ to $C_{12}$, such as xylene mixtures or substituted naphthalenes, phthalic esters, such as dibutyl- or dioctylphthalate, aliphatic hydrocarbons, such as cyclohexane or paraffins, alcohols and glycols, as well as ethers and esters thereof, such as ethanol, ethylene glycol, ethylene glycol monomethyl or -ethyl ethers, ketones, such as cyclohexanone, strongly polar solvents, such as N-methyl-2-pyrrolidone, dimethylsulfoxide or dimethylformamide, as well as optionally epoxidised vegetable oils, such as epoxidised coconut oil or soybean oil; or water.

The solid carriers used, for example for dusts and dispersible powders, are as a rule natural mineral fillers, such as calcite, talcum, kaolin, montmorillonite or attapulgite. In order to improve the physical properties, it is also possible to add highly dispersed silicic acid or highly dispersed absorbent polymers. Suitable granulated adsorptive carriers are porous types, for example pumice, ground brick, sepiolite or bentonite; and suitable nonsorbent carriers are materials such as calcite or sand. There can also be used a great number of pre-granulated materials of inorganic or organic nature, such as in particular dolomite or ground plant residues.

Suitable surface-active compounds are, depending on the nature of the active substance of the formula I to be formulated, nonionic, cationic and/or anionic tensides having good emulsifying, dispersing and wetting properties. By 'tensides' are also meant mixtures of tensides.

Suitable anionic tensides are both so-called water-soluble soaps as well as water-soluble, synthetic, surface-active compounds.

Soaps which are applicable are the alkali metal, alkaline-earth metal or optionally substituted ammonium salts of higher fatty acids ($C_{10}$–$C_{22}$), for example the Na or K salts of oleic or stearic acid, or of natural fatty acid mixtures, which can be obtained for example from coconut oil or tallow oil. Also to be mentioned are the fatty acid-methyl-taurine salts.

So-called synthetic tensides are however more frequently used, particularly fatty sulfonates, fatty sulfates, sulfonated benzimidazole derivatives or alkylarylsulfonates. The fatty sulfonates or sulfates are as a rule in the form of alkali metal, alkaline-earth metal or optionally substituted ammonium salts, and contain an alkyl group having 8 to 22 C atoms, 'alkyl' including also the alkyl moiety of acyl groups, for example the Na or Ca salts of ligninsulfonic acid, of dodecylsulfuric acid ester or of a fatty alcohol sulfate mixture produced from natural fatty acids. Included among these are also the salts of sulfuric acid esters and sulfonic acids of fatty alcohol ethylene oxide adducts. The sulfonated benzimidazole derivatives preferably contain 2 sulfonic acid groups and a fatty acid group having 8-22 C atoms. Alkylarylsulfonates are for example the Na, Ca or triethanolamine salts of dodecylbenzenesulfonic acid, of dibutylnaphthalenesulfonic acid or of a naphthalenesulfonic acid-formaldehyde condenation product. Also suitable are corresponding phosphates, for example salts of the phosphoric ester of a p-nonylphenol-(4-14)-ethylene oxide adduct.

Suitable nonionic tensides are in particular polyglycol ether derivatives of aliphatic or cycloaliphatic alcohols, saturated or unsaturated fatty acids and alkylphenols, which contain 3 to 30 glycol ether groups and 8 to 20 carbon atoms in the (aliphatic) hydrocarbon radical and 6 to 18 carbon atoms in the alkyl moiety of the alkylphenols.

Further suitable nonionic tensides are the water-soluble polyethylene oxide adducts, which contain 20 to 250 ethylene glycol ether groups and 10 to 100 propylene glycol ether groups, with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit. Examples of nonionic tensides which may be mentioned are: nonylphenolpolyethoxyethanol, castor oil polyglycol ethers, polypropylene/polyethyleneoxy adducts, tributylphenoxypolyethoxyethanol, polyethylene glycol and octylphenoxypolyethoxyethanol. Suitable also are fatty acid esters of polyoxyethylenesorbitan, such as polyoxyethylenesorbitan-trioleate, or phospholipides.

In the case of the cationic tensides, they are in particular quaternary ammonium salts whih contain as N-substituents at least one alkyl group having 8 to 22 C atoms and, as further substituents, lower, optionally halogenated alkyl, benzyl or lower hydroxyalkyl groups. The salts are preferably in the form of halides, methyl sulfates or ethyl sulfates, for example stearyltrimethylammonium chloride or benzyldi(2-chloroethyl)ethylammonium bromide.

The tensides customarily used in formulation practice are described, inter alia, in the following publications:
"Mc Cutcheon's Detergents and Emulsifiers Annual", MC Publishing Corp., Ridgewood, N.J., 1979;
M. and J. Ash, "Encyclopedia of Surfactants", Vol. I–VI, Chemical Publishing Co., Inc. New York 1980–1981;
H. Stache, "Tensid Taschenbuch", 2nd Edition, C. Hanser Verlag, Munich and Vienna, 1981.

The agrochemical preparations contain as a rule 0.1 to 95%, especially 0.1 to 80%, of active ingredient of the formula I, 1 to 99.9% of a solid or liquid additive, and 0 to 25%, particularly 0.1 to 25% of a tenside.

EXAMPLE 1

Process for producing 2,4,6-trifluoro-5-trifluoromethylpyrimidine (intermediate)

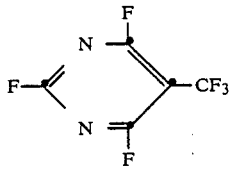

A 0.3-liter Monel autoclave is charged with 30.5 g of 2,4,6-trichloropyrimidine-5-carboxylic acid (0.134 mol), 144 g of sulfur tetrafluoride, $SF_4$ (1.3 mols) and 14.4 g of hydrofluoric acid, HF (0.72 mol), and is then heated for 7 hours at 110° C. and for 12 hours at 160° C. After cooling, the reagent is slowly blown out with cooling being applied. The residue is taken up in dichloromethane, and the solution is neutralised with saturated sodium bicarbonate solution. The mixture is subsequently filtered through Hyflo, and the aqueous phase is separated off and discarded. The organic phase is dried, and concentrated by evaporation to a volume of 50 ml. The residue is afterwards subjected to fractional distillation to finally isolate 5.3 g of an almost colourless liquid having high density and boiling point of 78° C. (19.5% of theory). The solvent first runnings, which boil at 37°–39° C., likewise contain portions of 2,4,6-trifluoro-5-trifluoromethylpyrimidine.

Analysis: $C_5F_6N_2$ M.W. 202.96
calculated: C: 29.72%;   F: 56.41; N: 13.87%; found: C: 29.07%; Cl: 1.57% F: 55.70%; N: 13.39%.

NMR spectrum: $^{19}F$-NMR ($CDCl_3$, hexafluorobenzene as internal standard; chemical displacements calculated on the basis of $CCl_3F$ as internal standard, $^{14}N$-decoupled):
58.3 ppm ($tJ_{F3C}$, $F\text{-}C(4.6)$ = 17.5 Hz, also $J_{F3C\text{-}F(2)}$ = 1 Hz:$CF_3$);
49.1 ppm ($qJ_{F\text{-}C(4.6)\text{-}F3C}$ = 17.5 Hz: F-C(4.6);
34.5 ppm (s: F-C(2))
cp. in this respect also J. Chem. Soc. (C) 1970, 1280.

EXAMPLE 2

Production of 2-amino-4,6-difluoro-5-trifluoromethylpyrimidine and 4-amino-2,6-difluoro-5-trifluoromethylpyrimidine (intermediates)

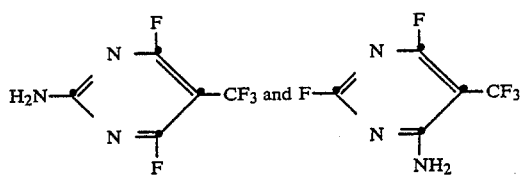

To a solution consisting of 2,4,6-trifluoro-5-trifluoromethylpyrimidine (which has been obtained according to Example 1 from 22.7 g of 2,4,6-trichloropyrimidine-5-carboxylic acid) in 100 ml of methylene chloride, are added at room temperature, with thorough stirring, 30 ml of 25% aqueous ammonia solution, a procedure resulting in a vigorous exothermic reaction. After further stirring for 10 minutes, the aqueous phase is separated; the organic phase is then washed with water, dried over sodium sulfate and concentrated by evaporation. The residue crystallises (16 g), and is subsequently dissolved and chromatographed with ether/hexane 1:1 through a 300 g silica gel column. There are finally isolated 3.8 g of the isomeric aminodifluoro-5-trifluoropyrimidine mixture, which contains the individual constituents in the ratio of 7:3 (determined by gas-chromatography) and which melts at 125°–155° C.

Yield: 44%, relative to the 2,4,6-trichloropyrimidine-carboxylic acid, in addition to an undetermined amount of 2,4-diamino-6-fluoro-5-trifluoromethylpyrimidine.

Analysis:
calculated: C: 30.16 H: 1.01 N: 21.11 F: 47.72; found: C: 30.18 H: 1.02 N: 21.08 F: 46.78.

EXAMPLE 3

Production of 2,4-diamino-6-fluoro-5-trifluoromethylpyrimidine

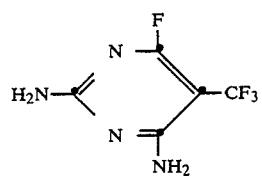

5.3 g of the mixture of 2-amino-4,6-difluoro-5-trifluoromethylpyrimidine and 4-amino-2,6-difluoro-5-trifluoromethylpyrimidine obtained from Example 2 (ratio 7:3, no correlation) are dissolved in 100 ml of tetrahydrofuran, and there are then added at room temperature, with stirring, 10 ml of 25% aqueous ammonia solution. The temperature firstly falls and then rises to 30° C. After further stirring for 30 minutes, ether is added to the reaction mixture; the organic phase is subsequently separated and is washed 3 times with water. It is afterwards dried over sodium sulfate and concentrated by evaporation. The residue is chromatographed with ether/hexane 1:1 through a 300 g silica gel column, and 4.75 g of 2,4-diamino-6-fluoro-5-trifluoromethylpyrimidine (91% of theory), m.p. 170°–174° C., are isolated.

Analysis: $C_5H_4F_4N_4$ (M.W. 196.11)
calculated: C: 30.62%; H: 2.06%; N: 28.57%; F: 38.75%; found: C: 31.01%; H: 2.04%; N: 28.44%; F: 38.05%.

There is also isolated 0.3 g (5% of theory) of a by-product subliming at 220°–225° C., which is identified, on the basis of the mass spectrum and of the analysis, as being 4,6-diamino-2-fluoro-5-trifluoromethylpyrimidine.

EXAMPLE 4

Production of 4-amino-2-methylamino-6-fluoro-5-trifluoromethylpyrimidine

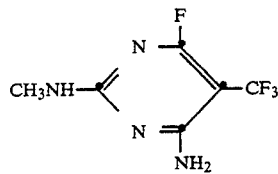

35 ml of 40% aqueous methylamine solution are added at room temperature, with vigorous stirring, to a solution of 2,4,6-trifluoro-5-trifluoromethylpyrimidine (produced according to Example 1 from 46 g of 2,4,6-trichloropyrimidine-5-carboxylic acid) in 200 ml of methylene chloride. After the addition has been completed, stirring is continued for 10 minutes, and the aqueous phase is then separated. The organic phase is concentrated by evaporation; the residue is subsequently taken up in 150 ml of tetrahydrofuran, and there are then added at room temperature, with stirring, 40 ml of a 40% aqueous ammonia solution. When the exothermic reaction has subsided, after about 75 minutes, ether is added to the reaction mixture, and the aqueous phase is separated; the organic phase is washed with water, dried, and concentrated by evaporation. The residue is purified by chromatography through a 2 kg silica gel column with ether/hexane 1:1. There are thus obtained 3 compounds, which are isolated individually.

The main fraction consists of 13.5 g of 4-amino-2-methylamino-6-fluoro-5-trifluoromethylpyrimidine (32% of theory, relative to 2,4,6-trichloropyrimidine-5-carboxylic acid), which are obtained as crystals, m.p. 160°–162° C.

$^{13}$C-NMR (DMSO-Cl$_6$) inter alia $\delta_{CH_3}$ 28.0 ppm
Analysis: $C_6H_6F_4N_4$ (M.W. 210.13)
calculated: C: 34.30%; H: 2.88%; N: 26.67%; F: 36.17%; found: C: 34.29%; H: 2.83%; N: 26.52%; F: 34.97%.

A second fraction consists of 3.2 g of 2-amino-4-methylamino-6-fluoro-5-trifluoromethylpyrimidine (7.5% of theory, relative to 2,4,6-trichloropyrimidine-5-carboxylic /acid), which melts at 100°–105° C. and is identified by the NMR spectrum and the analysis.

Obtained as the third fraction are 2.3 g of 2,4-bis-methylamino-6-fluoro-5-trifluoromethylpyrimidine (5% of theory, relative to 2,4,6-trichloropyrimidine-5-carboxylic acid), which melts at 142°–145° C. and is identified by the NMR spectrum and the analysis.

The following compounds are produced in a manner analogous to that of Examples 3 and 4:

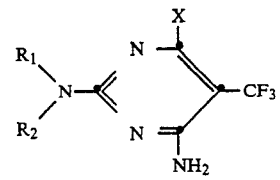

| No. | X | R$_1$ | R$_2$ | |
|---|---|---|---|---|
| 1 | F | H | H | m.p. 170–174° C. Ex. 3 |
| 2 | F | CH$_3$ | H | m.p. 160–162° C. Ex. 4 |
| 3 | F | CH$_3$ | CH$_3$ | m.p. 145° C. |
| 4 | F | C$_2$H$_5$ | H | |
| 5 | F | C$_3$H$_7$n | H | |
| 6 | F | cyclopropyl | H | |
| 7 | F | C$_2$H$_5$ | C$_2$H$_5$ | |
| 8 | F | C$_4$H$_9$n | H | |
| 9 | F | C$_4$H$_9$iso | H | |
| 10 | F | C$_4$H$_9$t | H | |
| 11 | F | C$_6$H$_{13}$n | H | |
| 12 | F | cyclopentyl | H | |
| 13 | F | cyclohexyl | H | |
| 14 | F | C$_3$H$_7$n | C$_3$H$_7$n | |
| 15 | F | C$_3$H$_7$iso | H | |
| 16 | F | C$_4$H$_9$sec | H | |
| 17 | F | cyclobutyl | H | |
| 18 | F | —C$_5$H$_{10}$— | | |
| 19 | F | —C$_4$H$_8$— | | |
| 20 | F | —C$_3$H$_6$— | | |

EXAMPLE 5

Production of 2,4,6-trichloropyrimidine-5-carboxylic acid (intermediate)

To a solution of 63.3 g (0.3 mol) of 2,4,6-trichloro-5-formylpyrimidine in 300 ml of fuming sulfuric acid (SO$_3$ content 25%) are added in flake form 24 g (0.24 mol) of chromium trioxide, and the mixture is stirred for 20 hours. The temperature rises within about one hour to 45°–50° C., and then falls again to room temperature (20°–25° C.). The reaction solution is poured into ice water, and the precipitate is filtered off and washed with a small amount of ice-water. The reaction product is dissolved in diethyl ether; the solution is then dried over sodium sulfate and subsequently evaporated to dryness. The yield is 55.4 g (81.2%) of 2,4,6-trichloropyrimidine-5-carboxylic acid, m.p. about 150° C. The melting point can be raised to 155°–157° C. by recrystallisation of the product from chloroform.

Analysis for $C_5HCl_3N_2O_2$ (molecular weight 227.43):
calculated: C: 26.41; H: 9.45; N: 12.32; O: 14.07; Cl: 46.77%; found: C: 26.28; H: 9.48; N: 12.23; O: 14.69; Cl: 45.93%. $^{13}$C-NMR spectrum (CD$_3$CN, TMS internal standard): 163.04 ppm (COOH), 160.2 ppm (C(4)) and (C(6)), 159.9 ppm (C(2)), 127.8 ppm (C(5)).

The starting product used in the above Example can be produced by the process described in the German Offenlegungsschrift No. 2,310,334.

2,4,6-Trichloropyrimidine-5-carboxylic acid can be produced by the process described above also under the following reaction conditions:

| Oxidising agent | Reaction medium | Yield of 2,4,6-tri chloropyrimidine-5-carboxylic acid |
|---|---|---|
| CrO$_3$ | 98% H$_2$SO$_4$ | 50% of theory |
| CrO$_3$ | fuming H$_2$SO$_4$ (SO$_3$ content 65%) | 60% of theory |
| K$_2$Cr$_2$O$_7$ | fuming H$_2$SO$_4$ (SO$_3$ content 25%) | 20% of theory |

EXAMPLE 6

2,4,6-Trichloropyrimidine-5-carboxylic acid (intermediate)

19.8 g (0.1 mol) of 5-methyl-2,4,6-trichloropyrimidine are introduced into 100 ml of fuming sulfuric acid (SO$_3$ content 25%), and with heating to 38° C. the solid substance goes into solution. There are then added 15.8 g (0.15 mol) of 95% chromium trioxide in flake form, and the reaction mixture is kept at 45°–50° C. by occasional slight cooling. The exothermic reaction has subsided after 2 hours. The suspension is stirred for a further 15 hours at 45°–50° C., and then dropped onto 200 g of ice, the temperature being held at a maximum of 5° C. by addition external cooling. The formed precipitate is filtered off, dried by suction, and dissolved in diethyl ether. The ether solution is dried over magnesium sulfate and evaporated to dryness. The yield is 5.2 g (23% of theory) of 2,4,6-trichloropyrimidine-5-carboxylic acid, m.p. 155°–157° C. The starting pyrimidine used in the above Example can be produced according to Chem. Ber. 90, 728 (1957).

EXAMPLE 7

The compounds of the formula I are not generally used as such in agriculture. Formulated compositions ready for use are employed and these can be used either directly or after being diluted with water.

Formulation Examples for liquid active ingredients of the formula I (%=percent by weight)

| 1. Emulsion concentrates | (a) | (b) | (c) |
|---|---|---|---|
| active ingredient | 25% | 40% | 50% |
| calcium dodecylbenzenesulfonate | 5% | 8% | 6% |
| castor oil-polyethylene glycol ether (36 mols of ethylene oxide) | 5% | — | — |
| tributylphenol-polyethylene glycol ether (30 mols of ethylene oxide) | — | 12% | 4% |
| cyclohexanone | — | 15% | 20% |
| xylene mixture | 65% | 25% | 20% |

Emulsions of any required concentration can be produced from concentrates of this type by dilution with water.

| 2. Solutions | (a) | (b) | (c) | (d) |
|---|---|---|---|---|
| active ingredient | 80% | 10% | 5% | 95% |
| ethylene glycol-monomethyl ether | 20% | — | — | — |
| polyethylene glycol M.W. 400 | — | 70% | — | — |
| N—methyl-2-pyrrolidone | — | 20% | — | — |
| epoxidised coconut oil | — | — | 1% | 5% |
| ligroin (boiling limits 160–190° C.) | — | — | 94% | — |

The solutions are suitable for application in the form of very fine drops.

| 3. Granulates | (a) | (b) |
|---|---|---|
| active ingredient | 5% | 10% |
| kaolin | 94% | — |
| highly dispersed silicic acid | 1% | — |
| attapulgite | — | 90% |

The active ingredient is dissolved in methylene chloride; the solution is subsequently sprayed onto the carrier, and the solvent is evaporated off in vacuo.

| 4. Dusts | (a) | (b) |
|---|---|---|
| active ingredient | 2% | 5% |
| highly dispersed silicic acid | 1% | 5% |
| talcum | 97% | — |
| kaolin | — | 90% |

Ready-for-use dusts are obtained by the intimate mixing together of the carriers with the active ingredient.

Formulation Examples for solid active ingredients of the formula I (%=percent by weight)

| 5. Wettable powders | (a) | (b) | (c) |
|---|---|---|---|
| active ingredient | 20% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7–8 mols of ethylene oxide) | — | 2% | — |
| highly dispersed silicic acid | 5% | 10% | 10% |
| kaolin | 67% | 27% | — |

The active ingredient is well mixed with the additives and the mixture is thoroughly ground in a suitable mill. Wettable powders which can be diluted with water to give suspensions of the required concentration are obtained.

| 6. Emulsion concentrates | |
|---|---|
| active ingredient | 10% |
| octylphenol polyethylene glycol ether (4–5 mols of ethylene oxide) | 3% |
| calcium dodecylbenzenesulfonate | 3% |
| castor oil polyglycol ether (36 mols of ethylene oxide) | 4% |
| cyclohexanone | 30% |
| xylene mixture | 50% |

Emulsions of the required concentration can be obtained from this concentrate by dilution with water.

| 7. Dusts | (a) | (b) |
|---|---|---|
| active ingredient | 5% | 8% |
| talcum | 95% | — |
| kaolin | — | 92% |

Dusts ready for use are obtained by mixing the active ingredient with the carriers and grinding the mixture in a suitable mill.

| 8. Extruder granulate | |
|---|---|
| active ingredient | 10% |
| sodium lignin sulfonate | 2% |
| carboxymethylcellulose | 1% |

-continued

| 8. Extruder granulate | |
|---|---|
| kaolin | 87% |

The active ingredient is mixed and ground with the additives, and the mixture is moistened with water. This mixture is extruded and then dried in a stream of air.

| 9. Coated granulate | |
|---|---|
| active ingredient | 3% |
| polyethylene glycol (M.W. 200) | 3% |
| kaolin | 94% |

The finely ground active ingredient is evenly applied, in a mixer, to the kaolin moistened with polyethylene glycol. Dustfree coated granulates are obtained in this manner.

| 10. Suspension concentrate | |
|---|---|
| active ingredient | 40% |
| ethylene glycol | 10% |
| nonylphenolpolyethylene glycol ether (15 mols of ethylene oxide) | 6% |
| sodium lignin sulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the additives. There is thus obtained a suspension concentrate from which can be produced, by dilution with water, suspensions of the concentration required.

EXAMPLE 8

Verification of herbicidal action (a) Pre-emergence test (pre-emergence action)

The seeds of *Avena sativa, Sinapis alba, Seteria italica* and *Stellaria media* are sown in pots about 11 cm in diameter in a greenhouse. Shortly afterwards, the surface of the soil is treated with an aqueous emulsion of the active ingredient, which has been prepared from a 25% emulsion concentrate. The amount sprayed onto the soil corresponds to 4 kg of active ingredient per hectare. The pots are then kept in the greenhouse at a temperature of 22°-25° C. with 50-70% relative humidity. The test is evaluated after 3 weeks, and the results are assessed on the basis of the following scale of ratings:

1 = plants have not germinated or have died,
2-3 = very strong action,
4-6 = medium action,
7-8 = slight action,
9 = no action (as in the case of the untreated control plants).

The results are as follows:

| | Compound No. | | |
|---|---|---|---|
| plant: | 1 | 2 | 3 |
| Avena sativa | 1 | 1 | 8 |
| Sinapis alba | 1 | 1 | 2 |
| Setaria italica | 1 | 1 | 3 |

-continued

| | Compound No. | | |
|---|---|---|---|
| plant: | 1 | 2 | 3 |
| Stellaria media | 1 | 1 | 2 |

(b) Post-emergence test (post-emergence action)

The plants *Avena sativa, Setaria italica, Lolium perenne, Solanum Lycopersicum, Sinapis alba, Stellaria media* and *Phaseolus vulgaris* are grown in pots 11 cm in diameter in a greenhouse until the plants have reached the 4–6 leaf stage, which is the case after about 2 weeks. They are then sprayed with an aqueous active-ingredient emulsion in a dosage corresponding to 4 kg of active ingredient per hectare, and are afterwards kept at 24°–26° C. with 45–60% relative humidity. The test is evaluated 15 days after the treatment, and the results are assessed according to the scale of ratings used in the pre-emergence test. The results are summarised in the following Table:

| | Compound No. | | |
|---|---|---|---|
| plant: | 1 | 2 | 3 |
| Avena sativa | 1 | 1 | 9 |
| Setaria italica | 1 | 1 | 5 |
| Lolium perenne | 2 | 2 | 7 |
| Solanum lycopersicum | 1 | 1 | 1 |
| Sinapis alba | 1 | 1 | 2 |
| Stellaria media | 1 | 1 | 2 |
| Phaseolus vulgaris | 5 | 3 | 7 |

Reduction of growth of grasses

Seeds of the grasses *Lolium perenne, Poa pratensis, Festuca ovina* and *Dactylis glomerata* are sown in a soil/peat/sand mixture (6:3:1) in plastic trays and watered in the customary manner. The emerged grasses are cut back each week to a height of 4 cm, and are sprayed 40 days after sowing and 1 day after the last cutting with an aqueous spray liquor of in each case an active ingredient of the formula I. The amount of active ingredient applied is equivalent of 5 kg of active ingredient per hectare. The growth of the grasses is assessed 10 and 21 days after application. The compounds 1, 2 and 3 reduce the growth of grass by between 13 and 22%.

Reduction of growth of cereals

Spring wheat (*Triticum aestivum*), Spring barley (*Hordeum vulgare*) and rye (Secale) are sown in sterilised soil in plastic trays and grown in a greenhouse. Five days after sowing, the cereal shoots are treated with a spray liquor of the active ingredient. The leaf application corresponds to 6 kg of active ingredient per hectare, and an assessment is made 21 days after the treatment. The compounds 1, 2 and 3 in this test reduce the growth of the cereal shoots by between 8 and 19%, relative to the growth of untreated shoots.

What is claimed is:

1. A 2,4-diamino-6-halo-5-trifluoromethylpyrimidine of the formula I

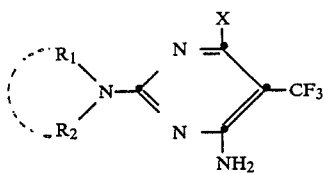

wherein

X is a halogen atom,

R$_1$ and R$_2$ independently of one another are each hydrogen, C$_1$–C$_6$-alkyl, C$_3$–C$_6$-cycloalkyl, or together form a C$_3$–C$_7$-alkylene bridge.

2. A 2,4-diamino-6-halo-5-trifluoromethylpyrimidine according to claim 1, wherein X is fluorine or chlorine.

3. A 2,4-diamino-6-fluoro-5-trifluoromethylpyrimidine according to claim 2.

4. 2,4-Diamino-6-fluoro-5-trifluoromethylpyrimidine according to claim 3.

5. 4-Amino-2-methylamino-6-fluoro-5-trifluoromethylpyrimidine according to claim 3.

6. 4-Amino-2-dimethylamino-6-fluoro-5-trifluoromethylpyrimidine according to claim 3.

7. A herbicidal and plant-growth-regulating composition containing as active ingredient an effective amount of a pyrimidine compound according to claim 1, together with carriers and/or other inert additives.

8. A method for selectively controlling weeds in crops of cultivated plants, which method comprises the pre-emergence treatment of the cultivated area or the post-emergence treatment of the crops with an effective amount of a pyrimidine compound according to claim 1.

9. A method for selectively controlling weeds in maize crops, which method comprises applying to said crops a herbicidally effective amount of a compound according to claim 1.

* * * * *